United States Patent [19]

Fischer et al.

[11] Patent Number: 4,459,414
[45] Date of Patent: Jul. 10, 1984

[54] TETRASUBSTITUTED PHTHALIC ACID DERIVATIVES, AND A PROCESS FOR THEIR PREPARATION

[75] Inventors: Walter Fischer, Reinach; Hans Zweifel, Basel, both of Switzerland

[73] Assignee: Ciba-Geigy Corporation, Ardsley, N.Y.

[21] Appl. No.: 363,188

[22] Filed: Mar. 29, 1982

[30] Foreign Application Priority Data

Apr. 8, 1981 [CH] Switzerland ............... 2364/81

[51] Int. Cl.³ ............... C07D 209/48; C07D 307/89; C07D 307/90
[52] U.S. Cl. ............... 548/473; 549/303; 549/310; 430/253; 430/927
[58] Field of Search ............... 548/471–473; 549/303; 430/927, 253, 270

[56] References Cited

U.S. PATENT DOCUMENTS

| | | | |
|---|---|---|---|
| 3,712,814 | 1/1973 | Ranz et al. | 430/270 |
| 3,850,964 | 11/1974 | Williams | 549/232 |
| 3,850,965 | 11/1974 | Williams | 549/232 |
| 3,867,404 | 2/1975 | von der Crone et al. | 548/460 |
| 3,884,955 | 5/1975 | von der Crone et al. | 548/471 |
| 3,922,284 | 11/1975 | Heath et al. | 548/476 |
| 4,079,041 | 3/1978 | Baumann et al. | 430/270 |
| 4,250,096 | 2/1981 | Kvita et al. | 430/270 |
| 4,363,917 | 12/1982 | Fischer et al. | 548/480 |

FOREIGN PATENT DOCUMENTS

| | | | |
|---|---|---|---|
| 1597 | 5/1979 | European Pat. Off. | 430/270 |
| 121436 | 3/1979 | Japan | 430/270 |

OTHER PUBLICATIONS

Rubner et al., "Photographic Sci. and Engin.", vol. 23(5), Sep./Oct. 1979, pp. 303–309.

Primary Examiner—Donald G. Daus
Assistant Examiner—William A. Teoli, Jr.
Attorney, Agent, or Firm—Luther A. R. Hall

[57] ABSTRACT

Novel tetrasubstituted phthalic acid derivatives of the formula

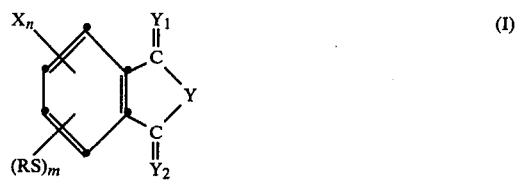

are described, in which $Y_1$ and $Y_2$ are oxygen and Y is

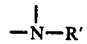

or —O—, or one of $Y_1$ and $Y_2$ is oxygen and the other is =N—R" and Y is —O—, and m, n, X, R, R' and R" are as defined in claim 1. The compounds (I) are suitable as sensitizers for photocrosslinkable polymers or as initiators for the photopolymerization of ethylenically unsaturated compounds or for the photochemical crosslinking of polyolefins.

9 Claims, No Drawings

TETRASUBSTITUTED PHTHALIC ACID DERIVATIVES, AND A PROCESS FOR THEIR PREPARATION

The present invention relates to novel tetrasubstituted phthalic acid derivatives, i.e. phthalic anhydrides, phthalic acid imides or phthalic acid isoimides, and a process for their preparation. The novel tetrasubstituted phthalic acid derivatives are used as sensitisers for photocrosslinkable polymers or as initiators, preferably in a mixture with amines, for the photopolymerisation of ethylenically unsaturated compounds or for the photochemical crosslinking of polyolefins.

Thioxanthones, which can be alkylated or halogenated, especially chlorinated, are amongst the best known and most effective sensitisers for photoinduced crosslinking reactions. A prerequisite for success in this type of application is a good compatibility of the sensitiser in the polymer, i.e. the sensitiser must be miscible with the polymer up to high concentrations. Furthermore, the sensitisers must be readily soluble in the solvents used in the processing of the polymers. The above-mentioned thioxanthones do not satisfy these requirements in every respect; in particular, they easily separate out in the polymer, whereby their sensitising action is greatly impaired.

It is also known that the photopolymerisation of ethylenically unsaturated compounds can be initiated by aromatic ketones of the benzophenone, anthraquinone, xanthone and thioxanthone type. Furthermore, it is known from U.S. Pat. No. 3,759,807 that the initiating action of such aromatic ketones can be accelerated by the addition of organic amines. Because these amines by themselves do not generally have any initiating action, they act in combination with aromatic ketones as activators or accelerators. This is of great industrial importance because the rate of production of photochemically hardened coatings or printing inks depends primarily on the rate of polymerisation of the unsaturated compound.

Novel tetrasubstituted phthalic acid derivatives of the formula I

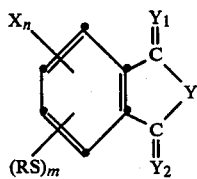

have now been found, in which m is an integer from 1 to 4, n is 0, 1, 2 or 3 and the sum of m+n is 4, $Y_1$ and $Y_2$ are oxygen and Y is

or —O—, or one of $Y_1$ and $Y_2$ is oxygen and the other is =N—R″ and Y is —O—, X is a halogen atom, especially chlorine or bromine, the radicals R (in the case where m>1) independently of one another are $C_1$-$C_{20}$-alkyl, $C_{3-5}$-alkenyl, $C_{3-5}$-alkynyl, $C_{2-4}$-monohydroxyalkyl, 2,3-dihydroxy-prop-1-yl, —CH₂COOH, —CH₂COO—$C_{1-4}$-alkyl, $C_{2-12}$-halogenoalkyl, benzyl, $C_{5-12}$-cycloalkyl, phenyl, halogenophenyl, nitrophenyl, alkylphenyl or alkoxyphenyl each having 1–4 C atoms in the alkyl or alkoxy, monohydroxyphenyl, monoaminophenyl or monoacetylaminophenyl, and R′ is hydrogen, $C_{1-20}$-alkyl, $C_{2-5}$-alkenyl, $C_{3-5}$-alkynyl, $C_{5-10}$-cycloalkyl, benzyl, phenyl, toluyl, $C_{2-8}$-monohydroxyalkyl, a saturated or unsaturated aliphatic $C_{1-4}$-carboxylic acid ester of $C_{2-8}$-monohydroxyalkyl, a $C_{1-12}$-alkyl ether of $C_{2-8}$-monohydroxyalkyl, —N($C_{1-4}$-alkyl)₂,

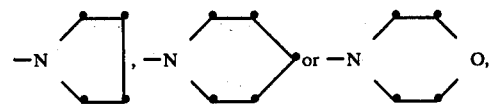

and R″ can have the same definition as R′, but is not hydrogen.

The compounds of the formula I are outstandingly suitable for use as sensitisers for photocrosslinkable polymers. They are distinguished, in particular, by a good compatibility with the polymer, a good solubility in customary organic solvents and a high photosensitivity. Moreover, the UV absorption can be influenced in such a way that the compounds according to the invention exert a sensitising action even on irradiation with long-wave UV light (up to about 450 nm) and thus effect the crosslinking of the photosensitive polymer. Photosensitising phthalimides and phthalic anhydrides with donors in the 3- to 6-positions were hitherto unknown.

The compounds of the formula I are also suitable, preferably in a mixture with organic amines, as initiators for the photopolymerisation of ethylenically unsaturated compounds or for the photochemical crosslinking of polyolefins.

Alkyl, monohydroxyalkyl, halogenoalkyl, alkenyl and alkynyl groups R, R′ or R″ and also alkyl substituents in groups R, R′ or R″, of the type defined, can be straight-chain or branched. Halogenoalkyl groups R can be substituted by one or more halogen atoms such as chlorine or bromine and, in particular, fluorine. Examples of alkyl, monohydroxyalkyl, —CH₂COO—$C_{1-4}$-alkyl, halogenoalkyl, alkenyl, alkynyl and —N($C_{1-4}$-alkyl)₂ groups of the type defined, and also esters of ethers of monohydroxyalkyl groups R, R′ or R″, of the type defined, are: methyl, ethyl, n-propyl, isopropyl, n-, sec.- and tert.-butyl, n-pentyl, 2- or 3-pentyl, n-hexyl, n-heptyl, 3-heptyl, n-octyl, n-decyl, n-dodecyl, n-tridecyl, n-tetradecyl, n-hexadecyl, n-octadecyl and eicosyl; 2-hydroxyethyl, 2- and 3-hydroxypropyl and 3- and 4-hydroxybutyl; —CH₂COOCH₃ and —CH₂COOC₂H₅; 2-chloroethyl, 2-bromoethyl, 2,2,2-trifluoroethyl, CH₂CH₂C₄F₉, —CH₂CH₂C₆F₁₃, —CH₂CH₂C₈F₁₇ and —CH₂CH₂C₁₀F₂₁; vinyl, allyl, methallyl, but-2-enyl and pent-4-enyl; prop-2-ynyl, but-3-ynyl and pent-4-ynyl; N,N-dimethylamino, N,N-diethylamino, N-methyl-N-ethylamino, N,N-di-n-propylamino and N,N-di-n-butylamino; and —CH₂CH₂OCOCH₃, —CH₂CH₂CH₂OCOC₂H₅, —CH₂CH₂OCO—n—C₄H₉, =CH₂CH₂OCOCH=CH₂, —CH₂CH₂OCOC(CH₃)=CH₂, —CH₂CH₂OCOCH=CHCH₃, —CH₂CH₂OCH₃, —CH₂CH₂CH₂OC₂H₅, =CH₂CH₂O—n—C₄H₉ and —CH₂CH₂CH₂O—n—C₈H₁₇.

Alkyl groups R, R′ and R″ are preferably straight-chain and have 1=12 and in particular 1=10 C atoms. Preferred alkenyl and alkynyl groups are R, R′ or R″ are: vinyl (R′ or R″), allyl, methallyl, but-2-enyl and prop-2-ynyl. Halogenoalkyl groups R are preferably also straight-chain and have 1–10 C atoms. Particular preference is given to —CH$_2$CF$_3$ and, in particular, —CH$_2$CH$_2$C$_p$F$_{2p+1}$ with p=6, 8 or 10.

Examples of cycloalkyl groups R, R' or R'' are cyclopentyl, cyclohexyl, cyclooctyl and cyclododecyl. Cyclohexyl is preferred. p-Toluyl is particularly suitable as a toluyl group R' or R''.

Halogenophenyl, nitrophenyl, alkylphenyl and alkoxyphenyl groups R can be monosubstituted or polysubstituted. Phenyl groups having one or two of the said substituents are preferred. Examples of suitable halogen atoms are fluorine, bromine and, in particular, chlorine. Examples of groups of this type are: 3-chlorophenyl or 3-bromophenyl, 3,4-dichlorophenyl, 2,5-dichlorophenyl, 3,4-dibromophenyl and 4-chlorophenyl, 4-bromophenyl or 4-fluorophenyl; 3- or 4-nitrophenyl and 3,5-dinitrophenyl; o-, m- and p-toluyl, 3,4-dimethylphenyl, 4-ethylphenyl and 4-n-butylphenyl; and 2-, 3- or 4-methoxyphenyl, 3- and 4-ethoxyphenyl, 2,5-dimethoxyphenyl, 3,4-diethoxyphenyl, 4-n-propoxyphenyl, 4-isopropoxyphenyl and 4-n-butoxyphenyl.

Preferred compounds of the formula I are those in which Y, Y$_1$, Y$_2$, m and n are as defined under the formula I, X is chlorine or bromine, the radicals R (in the case where m>1) independently of one another are straight-chain C$_{1-12}$-alkyl, 2-hydroxyethyl, phenyl, p-toluyl, 2-, 3- or 4-methoxyphenyl, 4-chlorophenyl, 2,5-dichlorophenyl, 4-nitrophenyl, 4-acetylaminophenyl, 2- or 4-aminophenyl, 4-hydroxyphenyl or —CH$_2$CH$_2$C$_p$F$_{2p+1}$ with p=6, 8 or 10, and R' is hydrogen, straight-chain C$_{1-12}$-alkyl, C$_{5-6}$-cycloalkyl, benzyl, phenyl, toluyl or C$_{2-4}$-monohydroxyalkyl, and R'' can have the same definition as R', but is not hydrogen. Particularly preferably, in these compounds, the radicals R independently of one another are straight-chain C$_{1-12}$-alkyl, 2-hydroxyethyl, —CH$_2$CH$_2$C$_8$F$_{17}$, phenyl, p-toluyl, 2- or 4-methoxyphenyl, 4-chlorophenyl, 2,5-dichlorophenyl or 4-nitrophenyl, R' is hydrogen, straight-chain C$_{1-10}$-alkyl, phenyl, p-toluyl or 2-hydroxyethyl and R'' is straight-chain C$_{1-10}$-alkyl, phenyl, p-toluyl or 2-hydroxyethyl.

Very particularly preferred compounds of the formula I are those in which Y, Y$_1$, Y$_2$, m and n are as defined under the formula I, X is chlorine or bromine, the radicals R independently of one another are straight-chain C$_{1-12}$-alkyl, in particular C$_{1-10}$-alkyl, 2-hydroxyethyl, —CH$_2$CH$_2$C$_8$F$_{17}$, phenyl, p-toluyl, 2- or 4-methoxyphenyl, 4-chlorophenyl or 4-nitrophenyl, R' is hydrogen, straight-chain C$_{1-10}$-alkyl, especially C$_{1-4}$-alkyl, 2-hydroxyethyl or phenyl and R'' is phenyl. If m is 1, the group —SR is preferably bonded in the 4-position. In the case where m=2, the groups —SR are preferably bonded in the 4,5-positions and the radicals R each have the same definition. Further preferred compounds of the formula I are those with m=4, pairs of radicals R of the groups —SR bonded in the 3,6- and 4,5-positions each having the same definition or all four radicals R being identical groups.

The compounds of the formula I can be prepared in a manner known per se, for example by reacting a compound of the formula II

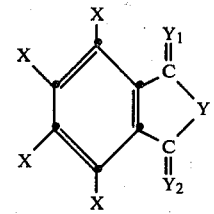

with one or more compounds of the formula III

or salts of compounds of the formula III, if appropriate reacting the resulting compounds of the formula I with n=1, 2 or 3 with a further compound of the formula III or a further salt thereof, and if appropriate isomerising compounds of the formula I in which one of Y$_1$ and Y$_2$ is oxygen and the other is =N—R'' and Y is —O—, to give the corresponding imides. In the formulae II and III, X, Y, Y$_1$, Y$_2$ and R are as defined under the formula I. The reaction with compounds of the formula III or salts thereof to give compounds of the formula I can accordingly be carried out directly or stepwise. Mixtures of various compounds of the formula I can also be formed by this process.

Salts with both inorganic and organic bases are suitable as salts of compounds of the formula III. Alkali metal salts and quaternary ammonium salts, such as the Na, K, tetramethylammonium, tetraethylammonium, benzyltrimethylammonium and benzyltriethylammonium salts, are preferred. The said salts can be used as such or be formed in situ in a manner known per se. Preferably, the compounds of the formula II are reacted, in the presence of a base, with a compound of the formula III. Bases which are advantageously used in this process are tertiary amines such as triethylamine or pyridine, and alkali metal acetates, bicarbonates or carbonates, in particular triethylamine and especially potassium carbonate. It is advantageous to use 1.0 to 3 equivalents of base, based on the compound of the formula III.

The above reaction can be carried out in an aqueous medium, but is advantageously carried out in the presence of an inert organic solvent, at temperatures between 0° C. and the boiling point of the solvent, preferably at 0°–30° C.

Examples of suitable inert organic solvents are aliphatic or aromatic hydrocarbons, which can be chlorinated, such as methylene chloride, 1,1,2,2-tetrachlorethane, chloroform, benzene, toluene, xylenes, chlorobenzene or dichlorobenzenes; aliphatic and cyclic ethers such as diethyl ether, diisopropyl ether, di-n-butyl ether, 1,2-dimethoxyethane, tetrahydrofuran and dioxane; alkyl esters of aliphatic monocarboxylic acids having a total of 2–8 C atoms, such as methyl, ethyl and n-butyl acetates and ethyl and n-butyl butyrates; N,N-dialkylamides of aliphatic monocarboxylic acids having 1–3 C atoms in the acid moiety, such as N,N-dimethylformamide and N,N-dimethylacetamide; cyclic amides such as N-methylpyrrolidone; dialkyl sulfoxides such as dimethyl sulfoxide; aliphatic ketones such as acetone and methyl ethyl ketone; alkylnitriles having 2–5 C atoms, such as acetonitrile and propionitrile; hexamethylphosphoric acid triamide; and alkanols having up to 6 C atoms, such as methanol, ethanol, propanol, isopropanol, n-butanol, isobutanol and tert.-butanol. Preferred solvents are 1,1,2,2-tetrachloroethane and, in particular, tetrahydrofuran and N,N-dimethylformamide.

If the starting compounds of the formula II are imides, the reaction with the compounds of the formula III or their salts can also be carried out in a two-phase mixture using a phase-transfer catalyst. In this process, the aqueous phase is advantageously rendered alkaline (pH 7-14) with, for example, $HCO_3^-$, $CO_3^{2-}$ or $OH^-$. The organic phase consists of a water-immiscible inert organic solvent, for example methylene chloride, chloroform, toluene or chlorobenzene. Phase-transfer catalysts which are advantageously used are tetraalkylammonium or tetraalkylphosphonium salts, for example benzyltriethylammonium chloride, cetyltrimethylammonium chloride or tetrabutylphosphonium chloride. In this process, the reaction temperatures are preferably between 0° C. and 150° C.

Compounds of the formula I in which $Y_1$ and $Y_2$ are oxygen and Y is —NH— or —O— can also be obtained by reacting a compound of the formula IV

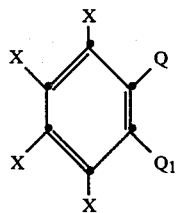

(IV)

in which X is as defined under the formula I and Q and $Q_1$ independently of one another are —CN or a carboxylic acid ester group, preferably a lower carboxylic acid alkyl ester group, directly or stepwise, with a salt of a compound of the formula III, in the manner indicated above. The compounds of the formula V

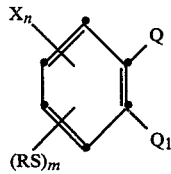

(V)

thus obtained are then hydrolysed in the customary manner, under acid or basic conditions, and cyclised. The cyclisation takes place spontaneously in some cases, in particular to give the anhydrides, or is carried out by heating or the addition of customary dehydrating agents.

If desired, the anhydrides of the formula I obtained by the above processes can be reacted with amines $H_2N$—R' or $H_2N$—R" to give the corresponding amic acids, which can be cyclised in a manner known per se to give imides or isoimides. The cyclisation to give imides of the formula I is generally carried out by simply heating or by using customary dehydrating agents such as acetic anhydride. The cyclisation to give isoimides of the formula I can be carried out, for example, by the processes described in the U.S. Pat. Nos. 2,995,577, 2,998,429, 3,035,065 and 4,179,444. Examples of suitable dehydrating agents for the conversion to isoimides of the formula I are ketene, carbodiimides, trifluoroacetic anhydride, chloroacetyl chloride or dichloroacetyl chloride, if appropriate in a mixture with tertiary amines. Isoimides of the formula I are preferably prepared by this method.

The isomerisation, in all cases, of the isoimides of the formula I to give corresponding imides can also be carried out in a manner known per se, for example by simply heating or by the processes described in U.S. Pat. Nos. 2,980,694 and 4,132,751, for example by treatment with alkali metal or ammonium salts of lower fatty acids, such as sodium acetate or triethylammonium acetate, or with mixtures of tertiary amines and phenol.

The compounds of the formula I can be used as sensitisers for photocrosslinkable polymers of a wide variety of types. Polymers of these types are used, for example, for the production of printing plates for the offset printing process, for the production of photooffset lacquers, or for unconventional photography, for example for the production of photographic images by means of photopolymerisation or photocrosslinking. Such polymers are used, in particular, as so-called photoresists for the production of printed circuits by methods known per se. In this process, that side of the printed circuit board which is coated with the photosensitive layer is exposed through a negative transparency carrying the printed circuit image, and then developed, and the unexposed parts of the layer are then removed by means of developing liquid.

Any desired materials of which the photosensitivity (sensitivity towards actinic rays) can be increased by the use of the sensitisers according to the invention can be used as the polymers. The compounds of the formula I are very particularly suitable as sensitisers for polymers of the type described in German Offenlegungsschrift No. 2,626,769, i.e. polymers which contain photosensitive groups of the formula VI

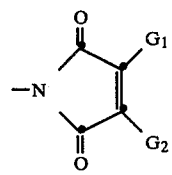

(VI)

in which $G_1$ and $G_2$ independently of one another are alkyl having 1-4 C atoms, especially methyl, or $G_1$ and $G_2$ together complete a five- to six-membered carbocyclic ring.

The compounds of the formula I can be incorporated into the photocrosslinkable polymers in a manner known per se. The content of sensitiser in the polymer can vary greatly, depending on the intended application and the number of photocrosslinkable groups present in the polymer, but is generally between about 0.1 and 20%, based on the weight of the polymer.

Finally, the compounds of the formula I are also applied as photoinitiators. The invention therefore also relates to the use of the said compounds, together with amines, as initiators for the photopolymerisation of ethylenically unsaturated compounds or for the photochemical crosslinking of polyolefins.

The organic amines used can be aliphatic, aromatic, araliphatic, cycloaliphatic or heterocyclic amines. They can be primary, secondary or tertiary amines. Examples of these are: butylamine, dibutylamine, tributylamine, cyclohexylamine, benzyldimethylamine, dicyclohexylamine, triethylamine, phenyl-diethanolamine, piperidine, piperazine, morpholine, pyridine, quinoline, ethyl p- dimethylaminobenzoate or Michler's ketone (4,4'-bis-dimethylaminobenzophenone).

Preferred mixtures are those of (A) a compound of the formula I in which m, n, X, R, R' and R" have the preferred definitions given above, and (B) an aliphatic tertiary amine, an alkyl p-dimethylaminobenzoate or Michler's ketone.

Examples of aliphatic tertiary amines are trimethylamine, triethylamine, triisopropylamine, tributylamine, dodecyldimethylamine, octyldimethylamine, triethanolamine, tris-(hydroxypropyl)-amine, N-methyldiethanolamine or N-butyldiethanolamine.

Particularly preferred mixtures are those of (A) a compound of the formula I in which m, n, X, R, R' and R" have the preferred definitions given above, and (B) triethanolamine or a $C_{1-4}$-alkyldiethanolamine.

Preferably, the said preferred mixtures contain the compounds of the formula I and the organic amines in a weight ratio of 4:1 to 1:4.

Examples of photopolymerisable compounds are unsaturated monomers such as acrylic or methacrylic acid esters, for example methyl, ethyl, n- or tert.-butyl, n-octyl or hydroxyethyl acrylate, methyl or ethyl methacrylate, ethylene diacrylate, butanediol diacrylate, hexanediol diacrylate, neopentyl diacrylate, trimethylolpropane trisacrylate, pentaerythritol tetraacrylate or pentaerythritol trisacrylate; acrylonitrile, methacrylonitrile, acrylamide, methacrylamide or N-substituted (meth)acrylamides; vinyl esters, for example vinyl acetate, propionate, acrylate or succinate; other vinyl compounds such as vinyl ethers, vinyl ketones, vinyl sulfones, styrene, alkylstyrenes, halogenostyrenes, divinylbenzene, N,N'-divinylurea, vinylnaphthalene, N-vinylpyrrolidone, vinyl chloride or vinylidene chloride; allyl compounds, such as diallyl phthalate, diallyl maleate, triallyl isocyanurate, triallyl phosphate or ethylene glycol diallyl ether, and mixtures of such unsaturated monomers. The mixtures according to the invention are particularly suitable for the photopolymerisation of acrylic acid esters and mixtures thereof.

Further examples are unsaturated acrylic resins. These include, for example, reaction products of polyepoxides (epoxide resins) with acrylic acid or methacrylic acid, or reaction products of polyisocyanates with hydroxyalkyl acrylates, and the reaction products of polyesters or polyethers containing hydroxyl groups with acrylic or methacrylic acid. These unsaturated acrylic resins are generally used in a mixture with one or more acrylates of a monohydric, dihydric or polyhydric alcohol, for example ethyl, butyl, benzyl, 2-ethylhexyl or 2-hydroxypropyl acrylate, ethylene glycol diacrylate, propylene glycol diacrylate, butanediol diacrylate, hexanediol diacrylate, trimethylolpropane trisacrylate or pentaerythritol tetraacrylate.

The invention also relates to photopolymerisable systems consisting of (a) at least one ethylenically unsaturated compound, (b) a mixture of (A) and (B) of the type defined, and if appropriate (c) other additives such as inhibitors, stabilisers, UV absorbers, fillers, pigments, dyes, thixotropic agents and flow control agents, for example silicone oil. Hydroquinone, hydroquinone derivatives, p-methoxyphenol or β-naphthols, for example, are used as inhibitors which are intended to protect against premature polymerisation, in particular during the preparation of the systems by mixing of the components. Examples of UV absorbers which can be used are those of the benzotriazole or benzophenone type. Examples of suitable fillers are silicic acid, talc or gypsum.

Preferred photopolymerisable systems are those of the type in which the proportions are 99.5–80% by weight of (a) and (c) and 0.5–20% by weight of (b), component (A) preferably consisting of a compound of the formula I in which m, n, X, R, R' and R" have the preferred definitions given above. An acrylic acid ester or a mixture of several acrylic acid esters is preferably used as component (a). It is also possible to use combinations with known photoinitiators which form radicals by photoinduced fragmentation, for example benzoin ethers, dialkoxyacetophenones or benzilketals.

The initiator mixtures according to the invention are of great importance for the photoinduced hardening of printing inks and white-pigmented layers, because the drying time of the binder is a decisive factor in the rate of production of graphic products and should be of the order of magnitude of fractions of a second. The initiators according to the invention are also suitable for photohardenable systems for the production of printing plates. A further field of use is the UV hardening of coatings for metal, for example in the lacquering of metal sheets for tubes, cans or bottle caps, and also the UV hardening of coatings for plastic, for example for PVC-based floor or wall coverings. Examples of the UV hardening for paper are the colourless lacquering of labels, record sleeves or book covers.

The mixtures according to the invention can also be used as initiators for the photochemical crosslinking of polyolefins. Examples of possible polyolefins are polypropylene, polybutene, polyisobutylene and copolymers, for example ethylene/propylene copolymers, but preferably polyethylene of low, medium or high density. The addition of the photoinitiators to the photopolymerisable systems is generally carried out by simply stirring them in, because the majority of these systems are liquid or readily soluble. This generally results in dissolution of the initiators, which ensures their uniform distribution and also the transparency of the polymers. The polymerisation is carried out by the known methods of photopolymerisation, by irradiation with light which contains a high proportion of short-wave radiation. Examples of suitable light sources are medium-pressure, high-pressure and low-pressure mercury vapour lamps, and also superactinic fluorescent tubes, the emission maxima of which are in the range between 250 and 450 nm. In the photochemical crosslinking of polyolefins, the photoinitiator is added to the polyolefin before or during the shaping treatment, for example by mixing it in as a powder or by mixing it with the plasticised polyolefin. The crosslinking is carried out by irradiation of the shaped article in solid form, for example in the form of sheets or fibres.

(A) Preparation Examples

EXAMPLE 1

4,5-Bis-(phenylthio)-3,6-dichlorophthalic anhydride and 4-phenylthio-3,5,6-trichlorophthalic anhydride 5.72 g (20 millimols) of tetrachlorophthalic anhydride, 4.84 g (44 millimols) of thiophenol, 6.08 g (60 millimols) of triethylamine and 50 ml of 1,1,2,2-tetrachloroethane are stirred at 60° C. for 18 hours. After evaporation, the residue is dissolved in 1N NaOH solution and the resulting solution is acidified and extracted with methylene chloride/acetone. After recrystallisation from toluene/cyclohexane under reflux, 2.41 g (30% of theory) of 4,5-bis-(phenylthio)-3,6-dichlorophthalic anhydride are obtained; melting point 204°14 7° C.

Analysis for $C_{20}H_{10}Cl_2O_3S_2$ (molecular weight 433.32): Calculated: C 55.44%, H 2.33%, Cl 16.37%, O 11.08%, S 14.80%. Found: C 55.05%, H 2.35%, Cl 16.29%, O 11.16%, S 14.83%.

0.91 g (13% of theory) of 4-phenylthio-3,5,6-trichlorophthalic anhydride is obtained from the mother liquor; melting point 162°–4° C.

Analysis for $C_{14}H_5Cl_3O_3S$ (molecular weight 359.61): Calculated: C 46.76%, H 1.40%, Cl 29.58%, O 13.35%, S 8.192%. Found: C 46.99%, H 1.42%, Cl 29.64%, O 13.44%, S 8.94%.

EXAMPLE 2

Tetrakis-(phenylthio)-phthalic anhydride 30.88 g (108 millimols) of tetrachlorophthalic anhydride, 48.79 g (443 millimols) of thiophenol, 91.06 g (659 millimols) of potassium carbonate and 300 ml of tetrahydrofuran are stirred under reflux for 3 hours. The mixture is evaporated and the residue is taken up in methylene chloride/2N HCl solution. The organic phase is separated off, dried over sodium sulfate and evaporated. After recrystallisation from toluene/cyclohexane, 44.71 g (71% of theory) of tetrakis-(phenylthio)-phthalic anhydride are obtained; melting point 141°–2° C.

Analysis for $C_{32}H_{20}O_3S_4$ (molecular weight 580.75): Calculated: C 66.18%, H 3.47%, S 22.08%. Found: C 66.25%, H 3.51%, S 21.97%.

EXAMPLE 3

4,5-Bis-(phenylthio)-3,6-dibromophthalic anhydride 2 g (4.31 millimols) of tetrabromophthalic anhydride, 0.975 g (8.84 millimols) of thiophenol, 2.41 g (17.47 millimols) of potassium carbonate and 20 ml of tetrahydrofuran are stirred at 0° C. for 2 hours and at 25° C. for 2 hours. The mixture is acidified with 2N HCl solution and extracted with tetrahydrofuran/toluene. The extracts are dried over sodium sulfate and evaporated. After recrystallisation from toluene/cyclohexane, 1.68 g (75% of theory) of 4,5-bis-(phenylthio)-3,6-dibromophthalic anhydride are obtained; melting point 183°–4° C.

Analysis for $C_{20}H_{10}Br_2O_3S_2$ (molecular weight 522.23): Calculated: C 46.00%, H 1.93%, Br 30.60%, S 12.28%. Found: C 46.25%, H 2.03%, Br 30.30%, S 12.19%.

EXAMPLE 4

4-Phenylthio-3,5,6-trichlorophthalic acid N-n-butylimide.

2 g (5.86 millimols) of tetrachlorophthalic acid N-n-butylimide are initially introduced, together with 2.43 g (17.59 millimols) of potassium carbonate, into 15 ml of tetrahydrofuran at 0° C. A solution of 680 mg (6.16 millimols) of thiophenol in 10 ml of tetrahydrofuran is added dropwise over a period of 2 hours. The mixture is stirred at 0° C. for 3 hours and gradually warmed to 25° C. over a period of 6 hours, and then acidified with 2N HCl solution and extracted with tetrahydrofuran/toluene. After drying over sodium sulfate, the organic phase is evaporated and the residue is recrystallised several times. This yields 0.17 g (7% of theory) of 4-phenylthio-3,5,6-trichlorophthalic acid N-n-butylimide; melting point 159°–63° C.

Analysis for $C_{18}H_{14}Cl_3NO_2S$ (molecular weight 414.73): Calculated: C 52.13%, H 3.40%, N 3.38%, S 7.73%. Found: C 52.36%, H 3.44%, N 3.39%, S 8.25%.

EXAMPLE 5

4,5-Bis-(phenylthio)-3,6-dichlorophthalic acid N-n-butylimide 20 g (58.65 millimols) of tetrachlorophthalic acid N-n-butylimide, 33.64 g (243 millimols) of potassium carbonate, 13.57 g (123 millimols) of thiophenol and 150 ml of tetrahydrofuran are stirred at 25° C. for 18 hours. The mixture is acidified and extracted with methylene chloride. The extracts are dried and evaporated. After recrystallisation from toluene/cyclohexane, 23.88 g (83% of theory) of 4,5-bis-(phenylthio)-3,6-dichlorophthalic acid N-n-butylimide are obtained; melting point 215°–6° C.

Analysis for $C_{24}H_{19}Cl_2NO_2S_2$ (molecular weight 488.45): Calculated: C 59.02%, H 3.92%, Cl 14.22%, N 2.87%, S 13.13%. Found: C 59.01%, H 3.98%, Cl 14.40%, N 3.22%, S 13.27%.

EXAMPLE 6

Tetrakis-(phenylthio)-phthalic acid N-n-butylimide 20 g (58.65 millimols) of tetrachlorophthalic acid N-n-butylimide, 26.49 g (240.5 millimols) of thiophenol, 49.04 g (355 millimols) of potassium carbonate and 200 ml of ethyl acetate are stirred at 25° C. for 18 hours and worked up as described in the preceding examples. After recrystallisation from toluene/cyclohexane, 35.99 g (97% of theory) of tetrakis-(phenylthio)-phthalic acid N-n-butylimide are obtained: melting point 159°–60° C.

Analysis for $C_{36}H_{29}NO_2S_4$ (molecular weight 635.87): Calculated: C 68.00%, H 4.60%, N 2.20%, S 20.17%. Found: C 67.99%, H 4.74%, N 2.25%, S 19.99%.

EXAMPLE 7

4-(p-Toluylthio)-3,5,6-trichlorophthalic acid N-2-hydroxyethylimide 2 g (6.08 millimols) of tetrachlorophthalic acid N-2-hydroxyethylimide, 0.79 g (6.38 millimols) of p-thiocresol, 2.52 g (18.24 millimols) of potassium carbonate and 20 ml of tetrahydrofuran are stirred at 25° C. for 20 hours. The mixture is acidified with dilute HCl solution and extracted with methylene chloride and the extracts are dried over sodium sulfate. After recrystallisation from toluene, 1.41 g (56% of theory) of the title compound are obtained: melting point 205°–9° C.

Analysis for $C_{17}H_{12}Cl_3NO_3S$ (molecular weight 416.71): Calculated: C 49.00%, H 2.90%, Cl 25.52%, N 3.36%, O 11.52%, S 7.69%. Found: C 49.15%, H 3.00%, Cl 25.30%, N 3.20%, O 11.49%, S 7.40%.

EXAMPLE 8

4,5-Bis(p-toluylthio)-3,6-dichlorophthalic acid N-2-hydroxyethylimide 20 g (60.8 millimols) of tetrachlorophthalic acid N-2-hydroxyethylimide, 15.86 g (127.67 millimols) of p-thiocresol, 34.03 g (246.22 millimols) of potassium carbonate and 200 ml of tetrahydrofuran are stirred at 25° C. for 2.5 days. The mixture is acidified and extracted with methylene chloride. After recrystallisation from toluene, 26.42 g (86% of theory) of the title compound are obtained; melting point 211°-2° C.

Analysis for $C_{24}H_{21}Cl_2NO_3S_3$ (molecular weight 506.46): Calculated: C 56.92%, H 4.18%, Cl 14.00%, N 2.76%, S 12.66%. Found: C 56.79%, H 3.98%, Cl 13.76%, N 2.84%, S 12.58%.

EXAMPLE 9

Tetrakis-(p-toluylthio)-phthalic acid N-2-hydroxyethylimide 2 g (6.08 millimols) of tetrachlorophthalic acid N-2-hydroxyethylimide, 3.1 g (24.93 millimols) of p-thiocresol, 5.08 g (36.78 millimols) of potassium carbonate and 20 ml of N,N-dimethylformamide are stirred at 25° C. for 1 hour. After evaporation, the residue is acidified with dilute HCl solution and extracted with methylene chloride. After recrystallisation from toluene/cyclohexane, 3.21 g (78% of theory) of the title compound are obtained; melting point 161°-2° C.

Analysis for $C_{38}H_{33}NO_3S_4$ (molecular weight 679.93): Calculated: C 67.13%, H 4.89%, N 2.06%, S 18.86%. Found: C 67.29%, H 4.97%, N 2.24%, S 18.55%.

EXAMPLE 10

Tetrakis-(p-nitrophenylthio)-phthalimide 2 g (7.02 millimols) of tetrachlorophthalimide, 4.36 g (28.08 millimols) of p-nitrothiophenol, 5.82 g (42.12 millimols) of potassium carbonate and 30 ml of tetrahydrofuran are stirred at 25° C. for 14 hours. The mixture is acidified and extracted with tetrahydrofuran/toluene and the extracts are dried and evaporated. The residue is washed with methylene chloride and recrystallised from dioxane/toluene. This yields 3.02 g (57% of theory) of tetrakis-(p-nitrophenylthio)-phthalimide; melting point 297°-301° C.

Analysis for $C_{32}H_{17}N_5O_{10}S_4$ (molecular weight 759.76): Calculated: C 50.59%, H 2.26%, N 9.22%, O 21.06%, S 16.88%. Found: C 50.60%, H 2.31%, N 9.10%, O 21.14%, S 16.79%.

EXAMPLE 11

Tetrakis-(p-methoxyphenylthio)-phthalic acid N-methylimide 2 g (6.7 millimols) of tetrachlorophthalic acid N-methylimide, 4.23 g (30.15 millimols) of p-methoxythiophenol, 6.25 g (45.2 millimols) of potassium carbonate and 20 ml of tetrahydrofuran are stirred at 25° C. for 4 hours. The mixture is acidified with 2N HCl solution and extracted with methylene chloride. The extracts are dried over sodium sulfate and evaporated. After recrystallisation from toluene/cyclohexane, 4.68 g (98% of theory) of the title compound are obtained: melting point 168°-70° C.

Analysis for $C_{37}H_{31}NO_6S_4$ (molecular weight 713.90): Calculated: C 62.25%, H 4.38%, N 1.96%, S 17.96%. Found: C 62.30%, H 4.40%, N 2.00%, S 17.40%.

EXAMPLE 12

4,5-Bis-(phenylthio)-3,6-bis-(p-nitrophenylthio)-phthalic acid N-n-butylimide 2 g (4.09 millimols) of 4,5-bis-(phenylthio)-3,6-dichlorophthalic acid N-n-butylimide, 1.46 g (9.41 millimoles) of p-nitrothiophenol, 2.55 g (18.45 millimols) of potassium carbonate and 20 ml of tetrahydrofuran are stirred at 50° C. for 20 hours. The mixture is cooled, acidified and extracted with methylene chloride. After recrystallisation from tetrahydrofuran, 1.9 g (78% of theory) of the title compound are obtained; melting point 175°-7° C.

Analysis for $C_{36}H_{27}N_3O_6S_4$ (molecular weight 725.87): Calculated: C 59.57%, H 3.75%, N 5.79%. Found: C 59.29%, H 3.82%, N 6.28%.

EXAMPLE 13

Tetrakis-(n-decylthio)-phthalic acid N-2-hydroxyethylimide 2 g (6.08 millimols) of tetrachlorophthalic acid N-2-hydroxyethylimide, 5.30 g (30.4 millimols) of n-decanthiol, 6.30 g (45.6 millimols) of potassium carbonate and 20 ml of N,N-dimethylformamide are stirred at 25° C. for 7 hours. The mixture is acidified and extracted with methylene chloride. After recrystallisation from n-hexane at 0° C., 3.75 g (70% of theory) of the title compound are obtained; melting point 57°-8° C.

Analysis for $C_{50}H_{89}NO_3S_4$ (molecular weight 880.51): Calculated: C 68.21%, H 10.19%, N 1.59%, S 14.56%. Found: C 68.15%, H 10.09%, N 1.70%, S 14.48%.

EXAMPLE 14

3,4,5-Tris-(p-chlorophenylthio)-6-bromophthalimide and 4,5-bis-(p-chlorophenylthio)-3,6-dibromophthalimide 2 g (4.46 millimols) of tetrabromophthalimide, 1.61 g (11.15 millimols) of p-chlorothiophenol, 2.31 g (16.73 millimols) of potassium carbonate and 20 ml of tetrahydrofuran are stirred at 25° C. for 14 hours. After acidification with dilute HCl solution, the mixture is extracted with tetrahydrofuran/toluene and the extracts are dried and evaporated. After recrystallisation from toluene/cyclohexane, 0.61 g (25% of theory) of 3,4,5-tris-(p-chlorophenylthio)-6-bromophthalimide is obtained; melting point 164°-9° C.

Analysis for $C_{26}H_{13}BrCl_3NO_2S_3$ (molecular weight 653.84): Calculated: C 47.76%, H 2.00%, Cl 16.27%, N 2.14%, O 4.89%, S 14.71%. Found: C 47.44%, H 2.26%, Cl 16.49%, N 2.42%, O 4.85%, S 14.70%.

0.15 g (6% of theory) of 4,5-bis-(p-chlorophenylthio)-3,6-dibromophthalimide is obtained from the mother liquor; melting point 310°-5° C.

Analysis for $C_{20}H_9Br_2Cl_2NO_2S_2$ (molecular weight 558.07): Calculated: C 40.71%, H 1.54%, Cl 12.01%, N 2.37%. Found: C 40.39%, H 1.77%, Cl 11.82%, N 2.69%.

EXAMPLE 15

Tetrakis-($\beta$-hydroxyethylthio)-phthalic acid N-2-hydroxyethylimide 2 g (6.08 millimols) of tetrachlorophthalic acid N-2-hydroxyethylimide, 2.14 g (27.36 millimols) of 2-mercaptoethanol, 5.46 g (39.52 millimols) of potassium carbonate and 20 ml of N,N-dimethylformamide are stirred at 25° C. for 4 hours. The mixture is acidified with dilute HCl solution and extracted with tetrahydrofuran/toluene. After drying over magnesium sulfate, the extracts are evaporated. When recrystallised from toluene/cyclohexane, the residue gives 0.74 g (24% of theory) of the title compound; melting point 152°-7°.

Analysis for $C_{18}H_{25}NO_7S_2$ (molecular weight 495.64): Calculated: C 43.62%, H 5.08%, N 2.83%. Found: C 43.35%, H 5.00%, N 3.23%.

EXAMPLE 16

3,6-Bis-(n-decylthio)-4,5-bis-(p-toluylthio)-phthalic acid N-2-hydroxyethylimide 2 g (3.95 millimols) of 4,5-bis-(p-toluylthio)-3,6-dichlorophthalic acid N-2-hydroxyethylimide, 1.51 g (8.69 millimols) of n-decane-1-thiol, 2.29 g (16.58 millimols) of potassium carbonate and 20 ml of N,N-dimethylformamide are stirred at 25° C. for 1 hour. After concentration, the residue is taken up in methylene chloride/dilute HCl solution. The extracts are dried over sodium sulfate and evaporated. After precipitation from n-hexane, 300 mg (10% of theory) of the title compound (waxy substance) are obtained.

Analysis for $C_{44}H_{61}NO_3S_4$ (molecular weight 780.22): Calculated: C 67.74%, H 7.88%, N 1.80%, S 16.44%. Found: C 67.61%, H 7.90%, N 1.82%, S 15.77%.

EXAMPLE 17

4-(p-Methoxyphenylthio)-3,5,6-trichlorophthalic acid N-methylimide 41.41 g (138 millimols) of tetrachlorophthalic acid N-methylimide, 19.42 g (138 millimols) of p-methoxythiophenol, 57.43 g of potassium carbonate and 410 ml of tetrahydrofuran are stirred at 25° C. for 24 hours. After evaporation, the residue is acidified and extracted with methylene chloride. After drying and evaporation, the residue is recrystallised from toluene. This yields 35.38 g (64% of theory) of the title imide; melting point 182°–6° C.

Analysis for $C_{16}H_{10}Cl_3NO_3S$ (molecular weight 402,68): Calculated: C 47.72%, H 2.50%, N 3.48%, S 7.96%, Cl 26.41%. Found: C 47.55%, H 2.55%, N 3.30%, S 8.26%, Cl 26.40%.

EXAMPLE 18

Tetrakis-(o-methoxyphenylthio)-phthalic acid N-phenylimide.

2 g (3.71 millimols) of tetrabromophthalic acid N-phenylimide, 2.34 g (16.7 millimols) of o-methoxythiophenol, 3.34 g (24.2 millimols) of potassium carbonate and 20 ml of tetrahydrofuran are stirred at 25° C. for 24 hours. After acidification, the mixture is extracted with methylene chloride, the extracts are dried and evaporated and the residue is recrystallised from toluene. This yields 2.75 g (96% of theory) of the title imide; melting point 142°–6° C.

Analysis for $C_{42}H_{33}NO_6S_4$ (molecular weight 775.97): Calculated: C 65.01%, H 4.29%, N 1.81%, S 16.53%. Found: C 65.18%, H 4.33%, N 1.85%, S 16.30%.

EXAMPLE 19

Tetrakis-(p-nitrophenylthio)-phthalic acid N-n-octylimide 1 g (1.32 millimols) of tetrakis-(p-nitrophenylthio)-phthalimide (prepared according to Example 10), 0.57 g (2.97 millimols) of 1-bromooctane, 0.68 g (4.96 millimols) of potassium carbonate and 10 ml of N,N-dimethylformamide are stirred at 25° C. for 5 hours. The mixture is concentrated and the residue is acidified and extracted with methylene chloride. After recrystallisation from toluene/cyclohexane, 1.02 g (89% of theory) of the title imide are obtained; melting point 202°–4° C.

Analysis for $C_{40}H_{33}N_5O_{10}S_4$ (molecular weight 871.97): Calculated: C 55.10%, H 3.82%, N 8.03%, S 14.71%. Found: C 55.05%, H 3.79%, N 8.13%, S 14.77%.

EXAMPLE 20

4,5-Bis-(ethylthio)-3,6-dichlorophthalic acid N-methylimide 3 g (10.04 millimols) of tetrachlorophthalic acid N-methylimide, 1.48 g (20.08 millimols) of ethanethiol, 5.55 g (40 millimols) of potassium carbonate and 30 ml of N,N-dimethylformamide are stirred at 0° C. for 4 hours. The mixture is taken up in water and acidified and the reaction product is filtered off. The residue is dissolved in tetrahydrofuran/toluene and the solution is dried and evaporated. After recrystallisation from toluene/cyclohexane, 1.75 g (63% of theory) of the title imide are obtained; melting point 154°–5° C.

Analysis for $C_{13}H_{13}Cl_2NO_2S_2$ (molecular weight 350.28): Calculated: C 44.58%, H 3.74%, Cl 20.24%, N 4.00%, S 18.30%. Found: C 44.56%, H 3.70%, Cl 20.24%, N 4.16%, S 18.16%.

EXAMPLE 21

4,5-Bis-(n-$C_8F_{17}$-$CH_2CH_2$-thio)-3,6-dichlorophthalimide 1 g (3.51 millimols) of tetrachlorophthalimide, 2.18 g (4.56 millimols) of n-$C_8F_{17}CH_2CH_2$-SH, 1.89 g (13.7 millimols) of potassium carbonate and 15 ml of N,N-dimethylformamide are stirred at 0° C. for 10 hours. The mixture is acidified and stirred with a large amount of water and the precipitate is filtered off and dissolved in tetrahydrofuran/toluene. The organic phase is washed with $NaHCO_3$ solution and saturated NaCl solution, dried over sodium sulfate and evaporated. After recrystallisation from toluene, 2.53 g (99% of theory) of the title imide are obtained; melting point 158°–61° C.

Analysis for $C_{28}H_9Cl_2F_{34}NO_2S_2$ (molecular weight 1172.34): Calculated: C 28.69%, H 0.77%, N 1.19%, S 5.47%. Found: C 28.68%, H 0.81%, N 1.33%, S 5.54%.

EXAMPLE 22

4-(p-Toluylthio)-3,5,6-trichlorophthalic acid N-methylimide 2 g (6.7 millimols) of tetrachlorophthalic acid N-methylimide, 950 mg (6.9 millimols) of potassium carbonate, 120 mg (0.33 millimol) of hexadecyltrimethylammonium bromide, 20 ml of xylene and 0.86 ml of water are stirred vigorously at 100° C. and a solution of 860 mg (6.9 millimols) of p-thiocresol in 20 ml of xylene is added dropwise over a period of 10 minutes. After 30 minutes, the mixture is cooled, acidified with 2N HCl solution and extracted with methylene chloride. After drying over sodium sulfate, evaporation and recrystallisation from toluene/cyclohexane, 310 mg (12% of theory) of the title imide are obtained; melting point 209°–16° C.

Analysis for $C_{16}H_{10}Cl_3NO_2S$ (molecular weight 386.68): Calculated: C 49.70%, H 2.61%, Cl 27.50%, N 3.62%, O 8.27%, S 8.29%. Found: C 49.76%, H 2.06%, Cl 27.35%, N 3.89%, O 8.38%, S 8.19%.

EXAMPLE 23

4,5-Bis-(phenylthio)-3,6-dichlorophthalic acid N-phenylisoimide 10.0 g (23 millimols) of 4,5-bis-(phenylthio)-3,6-dichlorophthalic anhydride and 100 ml of methylene chloride are initially introduced into a reaction vessel. A solution of 2.147 g (23 millimols) of aniline in 25 ml of diethyl ether is added dropwise, with stirring. After 18 hours of stirring and cooling, the reaction product is filtered off and dried. This yields 10.05 g (82% of theory) of 4,5-bis-(phenylthio)-3,6-dichlorophthalic acid mono-N-phenylamide; melting point 193°–200° C. (decomposition).

Analysis for $C_{26}H_{17}NS_2O_3Cl_2$ (molecular weight 526.45): Calculated: C 59.32%, H 3.25%, N 2.66%, S 12.18%, Cl 13.47%. Found: C 59.07%, H 3.30%, N 2.77%, S 11.87%, Cl 14.09%.

8.5 g (16 millimols) of 4,5-bis-(phenylthio)-3,6-dichlorophthalic acid mono-N-phenylamide and 40 ml of $CH_2Cl_2$ are initially introduced into a reaction vessel. 3.328 g (16 millimols) of dicyclohexylcarbodiimide in 20 ml of $CH_2Cl_2$ are then added dropwise. The mixture is stirred at 25° C. for 18 hours and filtered and the mother liquor is evaporated. After recrystallisation from methylene chloride/n-heptane, 7.9 g (97% of theory) of 4,5-bis-(phenylthio)-3,6-dichlorophthalic acid N-phenylisoimide are obtained; melting point 158°–160° C.

Analysis for $C_{26}H_{15}Cl_2S_2NO_2$ (molecular weight 508.44): Calculated: C 61.42%, H 2.97%, Cl 13.95%, N 2.76%, S 12.61%, O 6.29%. Found: C 61.25%, H 3.04%, Cl 14.23%, N 3.08%, S 12.40%, O 6.36%.

EXAMPLE 24

4-(p-Toluylthio)-3,5,6-trichlorophthalic acid N-methylimide 2 g (6.69 millimols) of tetrachlorophthalic acid N-methylimide are dissolved in 20 ml of xylene at 100° C.; 0.86 ml of water, 0.95 g of potassium carbonate and 120 mg of hexadecyltrimethylammonium bromide are added and a solution of 0.86 g (6.89 millimols) of p-thiocresol in 1 ml of xylene is added dropwise at 100° C. After 30 minutes, the mixture is cooled, acidified with 2N HCl solution and extracted with methylene chloride. The solution is dried with sodium sulfate and evaporated and the residue is recrystallised from toluene/cyclohexane. This yields 0.69 g (27%) of the title compound; melting point 212°–216°.

Analysis for $C_{16}H_{10}Cl_3NO_2S$ (molecular weight 386.68): Calculated: C 49.70%, H 2.61%, Cl 27.50%, N 3.62%, O 8.27%, S 8.29%. Found: C 49.76%, H 2.60%, Cl 27.35%, N 3.89%, O 8.38%, S 8.19%.

EXAMPLE 25

Tetrakis-(p-toluylthio)-phthalic anhydride 20 g (70 millimols) of tetrachlorophthalic anhydride, 37.36 g (301 millimols) of p-thiocresol, 60.91 g (441 millimols) of potassium carbonate and 200 ml of tetrahydrofuran are stirred under reflux for 2 hours. After evaporation, the residue is acidified with dilute HCl solution and extracted with methylene chloride. After recrystallisation from cyclohexane, 31.25 g (70%) of the title compound are obtained; melting point 129°–132°.

Analysis for $C_{36}H_{28}O_3S_4$ (molecular weight 636.86): Calculated: C 67.89%, H 4.43%, S 20.14%. Found: C 68.18%, H 4.39%, S 19.87%.

(B) Application example

(a) Preparation of the polymer

A polymer having the following structure and composition is prepared:

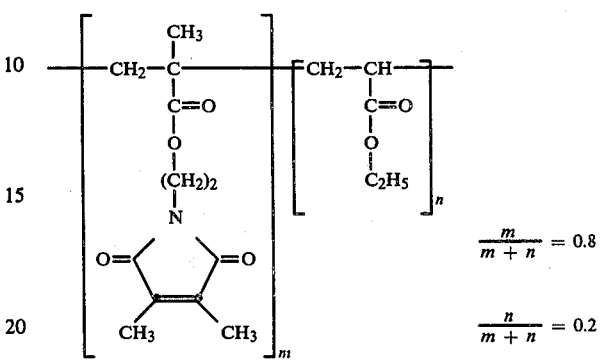

$$\frac{m}{m+n} = 0.8$$

$$\frac{n}{m+n} = 0.2$$

465.5 g (1.963 mols) of β-(dimethylmaleimidyl)ethyl methacrylate [prepared according to German Offenlegungsschrift 2,626,769] are dissolved, together with 49.15 g (0.49 mol) of ethyl acrylate, in 960 ml of 1-acetoxy-2-ethoxyethane, under nitrogen. A solution of 3.86 g of azoisobutyronitrile in 25 ml of 1-acetoxy-2-ethoxyethane is run in at 80° C., under a nitrogen atmosphere, and polymerisation is then allowed to proceed for 6 hours. While still hot, the solution is stabilised with 2.57 g of 2,6-di-tert.-butyl-p-cresol. The average molecular weight of the polymer thus obtained (determined by light scattering measurement in $CHCl_3$) is $3 \times 10^6$; intrinsic viscosity $\eta_{int}$: 0.8 dl/g ($CHCl_3$, 20° C.).

(b) Production of images $5 \times 10^{-3}$ mol of each of the sensitisers given in the table is added to 100 g of the polymer solution in 1-acetoxy-2-ethoxyethane, described above, diluted with N,N-dimethylformamide, the amount (concentration) of the sensitisers being based on the solids content. The polymer solutions containing the dissolved sensitiser are applied to copper-laminated epoxide plates, by whirler-coating (500 rpm for 1 minute), in such a way that, after drying (15 minutes at 80° C.), a 1–3μ thick polymer layer is formed on the copper. The coated plates are exposed through a negative original (step wedge: Stouffer 21-step-sensitivity-guide) with a 400 watt high-pressure mercury vapour lamp at a distance of 55 cm from the vacuum table, the vacuum table having an 8 mm thick Pyrex glass filter fitted in front.

After exposure, the image is developed in a 1,1,1-trichloroethane bath for 2 minutes, the non-crosslinked parts being dissolved away. The resulting relief image of the step wedge reproduced is revealed by etching the bare copper parts with 50% $FeCl_3$ solution. In the table which follows, $S_{rel}$ is the relative sensitivity. It is a factor which indicates by how much the exposure time must be longer or shorter than 3 minutes so that step 7 (optical density of the step wedge=1) is still reproduced. The following relationship applies:

$$S_{rel} = \frac{1}{\sqrt{2^{(7-x)}}},$$

X being the step which is actually reproduced after exposure for 3 minutes. The determination of $S_{rel}$ is based on the method described by W. S. De Forest ("Photoresist", McGraw Hill Book Company, New York, 1975, pages 113 et seq.) for determining the photosensitivity.

TABLE

| Compound of the formula I | λmax | ε | $S_{rel}$ |
|---|---|---|---|
| Tetrakis-(p-nitrophenylthio)-phthalic acid N—n-octylimide | 332 | 50,600 | 11.31 |
| 3,4,5-Tris-(p-chlorophenylthio)-6-bromophthalimide | 345 | 8,400 | 8.0 |
| 4,5-Bis-(phenylthio)-3,6-dichlorophthalic acid N—n-butylimide | 376 | 4,300 | 5.66 |
| 4-(p-Toluylthio)-3,5,6-trichlorophthalic acid N—2-hydroxyethylimide | 376 | 2,760 | 4.00 |
| Tetrakis-(p-nitrophenylthio)-phthalimide | 335 | 41,800 | 4.00 |
| 4-(p-Methoxyphenylthio)-3,5,6-trichlorophthalic acid N—methylimide | not determined | | 2.83 |
| 4-Phenylthio-3,5,6-trichlorophthalic acid N—n-butylimide | 370 | 3,000 | 2.83 |
| 4,5-Bis-(p-toluylthio)-3,6-dichlorophthalic acid N—2-hydroxyethylimide | 385 | 4,600 | 2.83 |
| 4,5-Bis-(phenylthio)-3,6-bis-(p-nitrophenylthio)-phthalic acid N—n-butylimide | 351 | 25,300 | 2.83 |
| Tetrakis-(phenylthio)-phthalic acid N—n-butylimide | 346 | 12,600 | 1.40 |
| Tetrakis-(o-methoxyphenylthio)-phthalic acid N—phenylimide | 348 | 11,000 | 1.40 |
| 4,5-Bis-(ethylthio)-3,6-dichlorophthalic acid N—methylimide | 380 | 2,100 | 1.00 |
| Tetrakis-(p-toluylthio)-phthalic acid N—2-hydroxyethylimide | 353 | 12,800 | 0.70 |
| Tetrakis-(p-methoxyphenylthio)-phthalic acid N—methylimide | 358 | 12,300 | 0.34 |
| 3,6-Bis-(n-decyl)-4,5-bis-(p-toluylthio)-phthalic acid N—2-hydroxyethylimide | 380 | 11,200 | 0.18 |
| Tetrakis-(β-hydroxyethylthio)-phthalic acid N—2-hydroxyethylimide | 380 | not determined | 0.13 |
| 4,5-Bis-(n-C$_8$F$_{17}$—CH$_2$CH$_2$—thio)-3,6-dichlorophthalimide | 340 | 2,300 | 0.13 |
| Tetrakis-(n-decylthio)-phthalic acid N—2-hydroxyethylimide | 310 | 11,800 | 0.01 |
| 4,5-Bis-(phenylthio)-3,6-dichlorophthalic anhydride | 380 | 5,100 | 4.00 |
| Tetrakis-(phenylthio)-phthalic anhydride | 355 | 13,600 | 1.00 |
| 4,5-Bis-(phenylthio)-3,6-dibromophthalic anhydride | 385 | 5,200 | 1.40 |
| 4,5-Bis-(phenylthio)-3,6-dichlorophthalic acid N—phenylisoimide | 377 | 10,800 | 5.66 |

What is claimed is:
1. A compound of the formula I

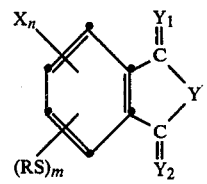

in which m is an integer from 1 to 4, n is 0, 1, 2 or 3 and the sum of m+n is 4, $Y_1$ and $Y_2$ are oxygen and Y is $$-\underset{|}{N}-R',$$

X is chlorine or bromine, the radical R is, or in the case where m>1 the radicals R independently of one another are, straight-chain $C_{1-12}$-alkyl, 2-hydroxyethyl, phenyl, p-toluyl, 2-, 3- or 4-methoxyphenyl, 4-chlorophenyl, 2,5-dichlorophenyl, 4-nitrophenyl, 4-acetylaminophenyl, 2- or 4-aminophenyl, 4-hydroxyphenyl or $-CH_2CH_2C_pF_{2p+1}$ with p=6, 8 or 10, and R' is hydrogen, straight-chain $C_{1-12}$-alkyl, $C_{5-6}$-cycloalkyl, benzyl, phenyl, toluyl or $C_{2-4}$-monohydroxyalkyl, with the proviso that when m is the integer 1, the group —SR is bonded in the 4-position; and when m is the integer 2, the groups —SR are bonded in the 4,5-positions and the radicals R are both identical.

2. A compound according to claim 1 wherein X is chlorine or bromine, the radical R is, or the radicals R independently of one another are, straight-chain $C_{1-12}$-alkyl, 2-hydroxyethyl, $-CH_2CH_2C_8F_{17}$, phenyl, p-toluyl, 2- or 4-methoxyphenyl, 4-chlorophenyl, 2,5-dichlorophenyl or 4-nitrophenyl, and R' is hydrogen, straight-chain $C_{1-10}$-alkyl, phenyl, p-toluyl or 2-hydroxyethyl.

3. A compound according to claim 1 wherein X is chlorine or bromine, the radical R is, or the radicals R independently of one another are, straight-chain $C_{1-12}$-alkyl, 2-hydroxyethyl, $-CH_2CH_2C_8F_{17}$, phenyl, p-toluyl, 2- or 4-methoxyphenyl, 4-chlorophenyl or 4-nitrophenyl, and R' is hydrogen, straight-chain $C_{1-10}$-alkyl, 2-hydroxyethyl or phenyl.

4. A compound of the formula I, according to claim 1, in which m is the integer 4 and pairs of radicals R of the groups —SR bonded in the 3,6- and 4,5-positions each have the same definition or all four radicals R are identical groups.

5. A compound, according to claim 1 which is 4-(p-toluylthio)-3,5,6-trichlorophthalic acid N-2-hydroxyethylimide.

6. A compound, according to claim 1 which is 4-(p-toluylthio)-3,5,6-trichlorophthalic acid N-methylimide.

7. A compound, according to claim 1, which is 4,5-bis-(phenylthio)-3,6-dichlorophthalic acid N-n-butylimide.

8. A compound, according to claim 1, which is tetrakis-(p-nitrophenylthio)-phthalic acid N-n-octylimide.

9. A compound, according to claim 1, which is 3,4,5-tris-(p-chlorophenylthio)-6-bromophthalimide.

* * * * *